US012708599B2

(12) United States Patent
Ebanks et al.

(10) Patent No.: US 12,708,599 B2
(45) **Date of Patent: *Aug. 18, 2026**

(54) LONG-WEAR COMPOSITIONS CONTAINING SILICONE ACRYLATE COPOLYMER AND GLYCEROLATED SILICONE RESIN

(71) Applicant: L'OREAL, Paris (FR)

(72) Inventors: Jody Ebanks, Clark, NJ (US); Tsang-Min Huang, Scotch Plains, NJ (US); Christopher Pang, Nanuet, NY (US)

(73) Assignee: L'OREAL, Paris (FR)

( * ) Notice: Subject to any disclaimer, the term of this patent is extended or adjusted under 35 U.S.C. 154(b) by 475 days.

This patent is subject to a terminal disclaimer.

(21) Appl. No.: 18/309,244

(22) Filed: Apr. 28, 2023

(65) Prior Publication Data

US 2024/0358623 A1 Oct. 31, 2024

(51) Int. Cl.
*A61K 8/895* (2006.01)
*A61K 8/892* (2006.01)
*A61Q 1/04* (2006.01)

(52) U.S. Cl.
CPC .............. *A61K 8/895* (2013.01); *A61K 8/892* (2013.01); *A61Q 1/04* (2013.01)

(58) Field of Classification Search
None
See application file for complete search history.

(56) References Cited

U.S. PATENT DOCUMENTS 10,744,074 B2 8/2020 El-Khouri
2004/0241126 A1 12/2004 Sakuta
2005/0008600 A1 1/2005 Nakanishi et al.
2006/0013790 A1 1/2006 Shimizu
2010/0266647 A1* 10/2010 Dingley .................. A61Q 1/02 424/59
2012/0014895 A1* 1/2012 Ikeda .................... A61K 8/891 424/78.03
2015/0366782 A1* 12/2015 Bui ......................... A61K 8/25 132/200
2020/0283628 A1 9/2020 Li et al.
2020/0283629 A1 9/2020 Li et al.
2020/0332065 A1* 10/2020 Abe ...................... A61K 8/894
2021/0401723 A1 12/2021 Ebanks et al.
2022/0175652 A1 6/2022 Watae et al.

FOREIGN PATENT DOCUMENTS

CN 104558616 B 2/2017
JP 3389271 B2 3/2003
JP 3533553 B2 5/2004

OTHER PUBLICATIONS

French Preliminary Search Report and Written Opinion issued Apr. 29, 2024, in French Application No. 2308060, with English translation of category of cited documents.
International Search Report and Written Opinion issued Aug. 26, 2024, in International PCT Application No. PCT/US2024/026374.

* cited by examiner

*Primary Examiner* — Danah Al-Awadi
(74) *Attorney, Agent, or Firm* — Womble Bond Dickinson (US) LLP

(57) ABSTRACT

Compositions including at least one silicone acrylate copolymer and at least one glycerolated silicone resin, as well as methods of applying such compositions to keratinous material, are provided.

16 Claims, No Drawings

LONG-WEAR COMPOSITIONS CONTAINING SILICONE ACRYLATE COPOLYMER AND GLYCEROLATED SILICONE RESIN

FIELD OF THE INVENTION

The present invention relates to compositions comprising (1) at least one silicone acrylate copolymer and (2) at least one glycerolated silicone resin. Among other improved or beneficial properties, these compositions have surprisingly good stability, long-wear, adhesion, and/or transfer-resistance properties.

DISCUSSION OF THE BACKGROUND

Many cosmetic compositions, including pigmented cosmetics such as foundations, mascaras and lipsticks, have been formulated in an attempt to possess long wearing properties upon application. Unfortunately, many of these compositions do not generally possess good long-wear/transfer-resistance properties as well as good application properties, good comfort properties and/or good appearance or stability properties (for example, consistency or uniformity in color over time).

For example, with respect to lip compositions, commercial products containing silicon resins such as MQ resins are known. Such products are known to provide good long wear properties and/or transfer-resistance. However, such products possess poor application properties and/or poor feel upon application (for example, feels rough). Therefore, a second composition (topcoat) is separately applied to such products to improve poor properties of the compositions to make the products acceptable to consumers. Furthermore, the topcoat composition must be reapplied continually so that the product remains acceptable to consumers, meaning that the products are effectively not "long-wearing" as they require constant maintenance and reapplication.

U.S. patent applications 2020/0283628 and 2020/0283629 relate compositions containing MQ resin having certain silanol requirements.

U.S. Pat. No. 10,744,074 relates to compositions capable of forming a multilayer structure after application which can contain silicone acrylates as well as other silicone compounds.

U.S. patent application 2021/0401723 relates to compositions capable of forming a multilayer structure after application which can contain T-modified MQ resin.

U.S. patent application 2020/0332065 relates to compositions containing glycerolated silicone resins.

There remains a need for improved compositions having improved cosmetic properties, particularly good stability, wear, transfer-resistance, adhesion, feel and/or appearance characteristics upon application.

Accordingly, one aspect of the present invention is a care and/or makeup and/or treatment composition for keratinous materials which has good cosmetic properties such as, for example, good stability, wear, transfer-resistance, adhesion, feel and/or appearance properties upon application.

SUMMARY OF THE INVENTION

The present invention relates to compositions comprising (1) at least one silicone acrylate copolymer and (2) at least one glycerolated silicone resin. Preferably, such compositions do not contain film-forming effective amounts of silicone resins which have not been glycerolated, and are preferably free of silicone resins which have not been glycerolated. Also preferably, such compositions are liquid.

The present invention also relates to anhydrous compositions comprising (1) at least one silicone acrylate copolymer and (2) at least one glycerolated silicone resin. Preferably, such compositions do not contain film-forming effective amounts of silicone resins which have not been glycerolated, and are preferably free of silicone resins which have not been glycerolated. Also preferably, such compositions are liquid.

The present invention also relates to colored compositions comprising (1) at least one coloring agent, (2) at least one silicone acrylate copolymer and (3) at least one glycerolated silicone resin. Preferably, such compositions do not contain film-forming effective amounts of silicone resins which have not been glycerolated, and are preferably free of silicone resins which have not been glycerolated. Also preferably, such compositions are liquid.

The present invention also relates to methods of treating, caring for and/or making up keratinous materials such as, for example, lips, skin or eyelashes, by applying compositions of the present invention to a keratinous material in an amount sufficient to treat, care for and/or make up the keratinous material.

The present invention also relates to methods of enhancing the appearance of keratinous materials such as, for example, lips, skin or eyelashes, by applying compositions of the present invention to a keratinous material in an amount sufficient to enhance the appearance of the keratinous material.

The present invention also relates to methods of increasing color stability of a colored composition comprising combining at least one silicone acrylate copolymer and at least one glycerolated silicone resin in the composition so as to increase color stability of the composition are provided. Preferably, such compositions are anhydrous. Preferably, such compositions do not contain film-forming effective amounts of silicone resins which have not been glycerolated, and are preferably free of silicone resins which have not been glycerolated. Also preferably, such compositions are liquid.

It is to be understood that both the foregoing general description and the following detailed description are exemplary/explanatory only and that they are not restrictive of the invention.

DETAILED DESCRIPTION OF THE INVENTION

As used herein, the expression "at least one" means one or more and thus includes individual components as well as mixtures/combinations.

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Film former", "film-forming polymer" or "film-forming agent" as used herein means a polymer or resin that leaves a film on the substrate to which it is applied, for example, after a solvent accompanying the film former has evaporated, absorbed into and/or dissipated on the substrate.

"Surfactant" and "emulsifier" are used interchangeably throughout this specification.

Other than in the operating examples, or where otherwise indicated, all numbers expressing quantities of ingredients and/or reaction conditions are to be understood as being modified in all instances by the term "about," meaning within 10% of the indicated number.

"Film former" or "film forming agent" as used herein means any material such as, for example, a polymer or a resin that leaves a film on the substrate to which it is applied.

"Polymer" as used herein means a compound which is made up of at least two monomers.

"Keratinous materials" includes materials containing keratin such as hair, skin, eyebrows, lips and nails.

"Substituted" as used herein (unless otherwise indicated), means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 115° C.

"Non-volatile", as used herein, means having a flash point of greater than about 115° C.

"Anhydrous" means the compositions contain less than 1% water. Preferably, the compositions of the present invention contain less than 0.5% water, and preferably no water (free of water).

"Transfer" as used herein refers to the displacement of a fraction of a composition which has been applied to a keratinous material by contact with another substrate, whether of the same nature or of a different nature. For example, when a composition such as a liquid lipstick has been applied, the composition can be transferred onto teeth or hands, or onto the cheek of another person. Irrespective of composition type, the composition can also transfer from the keratinous material to which it has been applied to another substrate such as napkins, collars, glasses, cups or other containers.

"Transfer-resistance" as used herein refers to the quality exhibited by a composition in resisting transfer. To determine transfer-resistance, the amount of composition transferred from a keratinous material to a substrate may be evaluated and compared. For example, a composition may be transfer-resistant if, after application to a keratinous material such as lips, skin or eyelashes and contact with a substrate, a majority of the composition is left on the wearer. Further, the amount transferred may be compared with that transferred by other compositions, such as commercially-available compositions. In a preferred embodiment of the present invention, little or no composition is transferred to the substrate from the keratinous material.

"Long wear" compositions as used herein refers to compositions where the compositions, after application to a keratinous material, do not transfer or smudge after contact with another substrate and retain a consistent appearance on the keratinous material for an extended period of time. "Long wear" compositions, as used herein can also refer to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to keratinous materials such as skin, eyelashes or lips and evaluating the color of the composition after an extended period of time. For example, the color of a composition may be evaluated immediately following application to the keratinous material and these characteristics may then be re-evaluated and compared after a certain amount of time. Further, these characteristics may be evaluated with respect to other compositions, such as commercially available compositions. Additionally, long wear properties may be evaluated by applying a sample, allowing it to dry, and then abrading the sample to determine removal/loss of sample.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase.

"Free" or "substantially free" or "devoid of" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of non-glycerolated silicone resin" means that an effective amount (that is, a film-forming effective amount) of non-glycerolated silicone resin is omitted from the composition (that is, about 0% by weight), "substantially free of non-glycerolated silicone resin" means that non-glycerolated silicone resin is present in amounts not greater than 0.1% by weight, and "devoid of non-glycerolated silicone resin" means that non-glycerolated silicone resin" is present in amounts not greater than 0.25% by weight, based on the total weight of the composition. The same nomenclature applies for all other ingredients identified throughout the application and in this paragraph such as, for example, wax (compositions of the invention which are "free of wax," "substantially free of wax," and "devoid of wax" have meanings consistent with the discussion within this paragraph), even if not specifically discussed for each identified ingredient. Discussed examples of the use of such language such as those in this paragraph are intended to be exemplary, not limiting.

"Physiologically acceptable" means compatible with keratinous material and having a pleasant color, odor and feel, and which does not cause any unacceptable discomfort liable to discourage a consumer from using the composition. Acceptable pH levels for compositions of the present invention are preferably acidic, that is, less than 7, preferably 6.5 or less, preferably 6.0 or less, preferably 5.5 or less, including all ranges and subranges therebetween such as, for example 3 to 5, 4 to 6, 3 to 4.5, etc. Compositions of the present invention may be in the form of a gel composition.

"Natural compound" refers to any compound derived directly from a natural substance such as a plant without having undergone any chemical modification.

"Compound of natural origin" refers to any compound derived from a natural compound which has undergone one or more chemical modifications, for example by organic synthesis reaction, without the properties of the natural compound having been modified.

"Synthetic compound" refers to any compound which is not a natural compound or a compound of natural origin.

"Room temperature" means 25° C.

"Atmospheric pressure" means 760 mmHg, i.e. 105 pascals.

"Liquid" means a composition which can conform to a container into which it is placed.

The compositions and methods of the present invention can comprise, consist of, or consist essentially of the essential elements and limitations of the invention described herein, as well as any additional or optional ingredients, components, or limitations described herein or otherwise useful. For example, the film forming system or film forming component can consist essentially of (1) the at least one silicone acrylate copolymer and (2) the at least one glycerolated silicone resin. Similarly, the oil system or oil component can consist essentially of silicone oils.

For purposes of the present invention, the "basic and novel property" associated with compositions, components and methods which "consist essentially of" identified ingredients or actions is "color stability after 6 months at room temperature, with or without centrifugation."

"Color stability after 6 months at room temperature" means the color of a composition remains uniform or homogeneous after 6 months at room temperature.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

All U.S. patents or patent applications disclosed herein are expressly incorporated by reference in their entirety.

Silicone Acrylate Copolymer

According to the present invention, compositions including at least one silicone acrylate copolymer are provided. Silicone acrylate copolymers are polymers containing siloxane group(s) and hydrocarbon group(s). For example, suitable polymers include polymers comprising a hydrocarbon backbone such as, for example, a backbone chosen from vinyl polymers, methacrylic polymers, and/or acrylic polymers and at least one chain chosen from pendant siloxane groups, and polymers comprising a backbone of siloxane groups and at least one pendant hydrocarbon chain such as, for example, pendant vinyl, methacrylic and/or acrylic group(s). Suitable silicone acrylate copolymers can comprise at least about 10%, 20%, 30%, 40%, 50%, 60%, 70%, 80%, or 90% silicone (siloxane groups) by weight, and can comprise at least about 10%, 20%, 30%, 40%, 50%, 60%, 70%, 80%, or 90% acrylate (hydrocarbon groups) by weight.

The at least one silicone acrylate copolymer can be chosen from silicone/(meth)acrylate copolymers, such as those as described in U.S. Pat. Nos. 5,061,481, 5,219,560, and 5,262,087, and U.S. patent application 2012/0301415, the entire contents of all of which are hereby incorporated by reference.

The at least one silicone acrylate copolymer may be selected from polymers derived from non-polar silicone copolymers comprising repeating units of at least one polar (meth)acrylate unit and vinyl copolymers grafted with at least one non-polar silicone chain. Non-limiting examples of non-dendrimer copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (INCI name: isododecane (and) acrylate/dimethicone copolymer), KP-561 (acrylates/stearyl acrylate/dimethicone acrylates copolymer), KP-562 (acrylates/behenyl acrylate/dimethicone acrylates copolymer), and mixtures thereof. Additional examples include the acrylate/dimethicone dendrimer copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Further non-limiting examples of such polymers and their synthesis are disclosed, for example, in U.S. Pat. Nos. 4,972,037, 5,061,481, 5,209,924, 5,849,275, and 6,033,650, and PCT applications WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other non-limiting examples of useful silicone acrylate copolymers include silicone/acrylate graft terpolymers, for example, the copolymers described in PCT application WO 01/32727, the disclosure of which is hereby incorporated by reference.

Other useful polymers can include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

The silicone acrylate copolymer preferably is present in the compositions of the present invention in an active solid content amount ranging from about 1% to about 35%, preferably from about 2.5% to about 30%, and preferably from about 5% to about 25%, by weight with respect to the total weight of the composition, including all ranges and subranges therebetween. It is to be understood that acceptable ranges of silicone acrylate copolymer present in invention compositions include 2%-15%, 10%-30%, 5%-35%, 20%-30%, 5%-15%, by weight based on the weight of the composition.

Glycerolated Silicone Resin

In accordance with the present invention, compositions comprising at least one glycerolated silicone resin are provided.

Preferably, compositions of the present invention comprise a film forming component comprising at least one glycerolated silicone resin, at least two glycerolated silicone resins, at least three glycerolated silicone resins, at least four glycerolated silicone resins, etc. Accordingly, film forming components of the present invention can contain, for example, any number of glycerolated silicone resins such as from 1 to 10 such resins, 1-5 such resins, 1-3 such resins, etc.

The term “glycerolated silicone resin” is understood to mean a resin which comprises, in its chemical structure, one or more monoglycerol or polyglycerol group(s).

According to preferred embodiments of the invention, the glycerolated silicone resin(s) is (are) preferably present in a content as active material ranging from 0.1% to 40% by weight, with respect to the total weight of the composition, preferably ranging from 1% to 30% by weight and more preferably from 5% to 15% by weight, with respect to the total weight of the composition, including all ranges and subranges therebetween such as 1% to 5%, 5% to 25%, 12.5% to 30%, 2% to 12.5%, etc.

The glycerolated silicone resin(s) according to the invention are preferably chosen from those of following formula (1):

$$(R^1_3SiO_{1/2})_a(R^2(CH_3)_2SiO_{1/2})_b(R^3SiO_{1/2})_c(R^1_2SiO_{2/2})_d(R^1SiO_{3/2})_e(SiO_{4/2})_f \quad (1)$$

in which each $R^1$, which are identical or different, is an alkyl, aryl or aralkyl group of 1 to 30≤carbon atoms, or a group substituted by a halogen, a group substituted by an amino or a group substituted by a carboxyl of the latter;

each $R^2$ is a mono- or polyglycerol group of following general formula (2)

$$—(CH_2)_2—C_lH_{2l}—O—(CH_2CH(OH)CH_2O)_iR^4 \quad (2)$$

in which $R^4$ is a substituted or unsubstituted monovalent hydrocarbon group or a hydrogen atom, and the indices I and i are numbers which satisfy the conditions $0 \leq I \leq 15$ and $0 < i \leq 5$, each $R^3$ is an identical or different group of general formula (3), of general formula (4), of general formula (5) or of general formula (6) below

[Chem 3]

$$—(CH_2)_2—C_mH_{2m}—(SiOR^1_2)]—SiR^1_3 \quad (3)$$

[Chem 4]

$$—(CH_2)_2—C_mH_{2m}—SiR^1_{k1}—(OSiR^1_3)_3\text{-}k_{1j} \quad (4)$$

[Chem 5]

$$—(CH_2)_2—C_mH_{2m}—SiR^1_{k1}—(OSiR^1_{k2}(OSIR^1_3)_{3-k2})_{3-k1} \quad (5)$$

[Chem 6]

$$—(CH_2)_2—C_mH_{2m}—SiR^1_{k1}—(OSiR^1_{k2}(OSiR^1_{k3}(OSiR^1_3)_{3-k3})_{3-k2})_{3-ka} \quad (6)$$

Where each $R^1$, which are identical or different, is an alkyl, aryl or aralkyl group of 1 to 30≤carbon atoms, or a group substituted by a halogen, a group substituted by an amino or a group substituted by a carboxyl of the latter;

the indices m, j and $k_1$ to $k_3$ are numbers which satisfy the conditions $0 \leq m \leq 5$, $0 \leq j \leq 500$, $0 \leq k1 \leq 2$, $0 \leq k_2 \leq 2$ and $0 \leq k_3 \leq 2$;

the indices a, b, c, d, e and f are numbers which satisfy the conditions $0 \leq a \leq 400$, $0 < b \leq 200$, $0 \leq c \leq 400$, $0 \leq d \leq 320$, $0 \leq e \leq 320$, $0 < f \leq 1000$ and $0.5 \leq (a+b+c)/f \leq 1.5$.

The glycerolated silicone resins according to the invention are described in the patent application US20200332065A1 of SHIN-ETSU.

According to a specific embodiment, the glycerolated silicone resin(s) of formula (1) as defined above are chosen from those for which the indices b and c satisfy the conditions $0 < b \leq 30$ and $0 \leq c \leq 30$;

the index i in the general formula (2) of the monoglycerol or polyglycerol group $R^2$ is a number which satisfies the condition $0 < i \leq 3$.

According to a specific embodiment, the glycerolated silicone resin(s) of formula (1) are in the solid form at 25° C. when the index c satisfies the condition $0 < c \leq 400$ and $R^3$ is a group of general formula (3) where the index j satisfies the condition $0 \leq j \leq 10$.

According to a specific embodiment, the glycerolated silicone resin(s) exhibit a weight-average molecular weight ranging from 1000 to 100,000.

The glycerolated silicone resin(s) according to the invention are amphiphilic, that is to say exhibit two parts of different polarities. In general, one is lipophilic (soluble or dispersible in an oily phase). The other is hydrophilic (soluble or dispersible in water). They are characterized by the value of their HLB (Hydrophilic-Lipophilic Balance), the HLB being the ratio of the hydrophilic part to the lipophilic part in the molecule. The term HLB is well known to a person skilled in the art and is described, for example, in “The HLB System. *A Time-Saving Guide to Emulsifier Selection*” published by ICI Americas Inc., 1984). The value of the HLB of the glycerolated silicone resins according to the invention preferably varies from 0.1 to 15 according to the Griffin method.

The glycerolated silicone resin(s) according to the invention can be obtained by a preparation process comprising the stage of hydrosilylation A) of a silicone resin containing a hydrosilyl group of formula (7) below $$(R^1_3SiO_{1/2})_a H_nR^1_{3-n}SiO_{1/2})_{b+c}(R^1_2SiO_{2/2})_d(R^1SiO_{3/2})_e(SiO_{4/2}) \quad (7)$$

in which:

each $R^1$, which are identical or different, is an alkyl, aryl or aralkyl group of 1 to 30≤carbon atoms, or a group substituted by a halogen, a group substituted by an amino or a group substituted by a carboxyl of the latter;

the indices a, b, c, d, e and f are numbers which satisfy the conditions $0 \leq a \leq 400$, $0 < b \leq 200$, $0 \leq c \leq 400$, $0 \leq d \leq 320$, $0 \leq e \leq 320$, $0 < f \leq 1000$ and $0.5 \leq (a+b+c)/f \leq 1.5$;

n is a number which satisfies a condition 1≤n 3, with

B) one or more compounds which are chosen from the compounds terminated by an alkenyl group of general formulae (8), (9), (10), (11) and (12) below $$CH_2{=}CH—C_lH_{2l}—O—(CH_2CH(OH)CH_2O)iR^4 \quad (8)$$

[Chem 9]

$$CH_2{=}CH—C_mH_{2m}—(SiOR^1_2)—SiR^1_3 \quad (9)$$

[Chem 10]

$$CH_2{=}CH—C_mH_{2m}—SiR^1_{k1}—(OSiR^1_3)_{3-k1} \quad (10)$$

[Chem 11]

$$CH_2{=}CH—C_mH_{2m},—SiR^1_{k1}—(OSiR^1_{k2}(OSiR^13)_{3-k2})_{3-k1} \quad (11)$$

[Chem 12]

$$CH_2{=}CH{-}C_mH_{2m}{-}SiR^1k^1{-}(OSiR^1_{k2}(OSiR^1_{k3}(OSiR^1_{k3})_{3\text{-}k3})_{3\text{-}k2})_{3\text{-}k1} \quad (12)$$

Where $R^4$ is a substituted or unsubstituted monovalent hydrocarbon group or a hydrogen atom, the indices I and i are numbers which satisfy the conditions $0 \le I \le 15$ and $0 < i \le 5$;

the indices m, j and $k_1$ to $k_3$ are numbers which satisfy the conditions $0 \le m \le 5$, $0 \le j \le 500$, $0 \le k_1 \le 2$, $0 \le k_2 \le 2$ and $0 \le k_3 \le 2$; said silicone resin containing a hydrosilyl group of formula (7) which reacts with at least one compound in the formula (8).

The hydrosilylation reaction is carried out in the presence, for example, of a platinum or rhodium catalyst. The preferred ranges for b, c, d, e, f, $R^4$, l, m, i, j and $k_1$ to $k_3$ are as defined above.

Process for the Preparation of the Glycerolated Silicone Resin

A specific example of process for the preparation of the glycerolated silicone resin according to the invention is described below.

As mentioned above, the glycerolated silicone resin according to the invention can be obtained by the stage of hydrosilylation (A) of a silicone resin containing a hydrosilyl group of mean formula (7) below:

$$(R^1_3SiO_{1/2})_a(H_nR^1_{3\text{-}n}SiO_{1/2})_{b+c}(R^1_2SiO_{2/2})_d(R_1SiO_{3/2})_e(SiO_{4/2})_f \quad (7)$$

in which each $R^1$ is an identical or different alkyl, aryl or aralkyl group of 1 to 30≤carbon atoms, or a group substituted by a halogen, a group substituted by an amino or a group substituted by a carboxyl of the latter;

the indices a, b, c, d, e and f are numbers which satisfy the conditions $0 \le a \le 400$, $0 < b \le 200$, $0 \le c \le 400$, $0 \le d \le 320$, $0 \le e \le 320$, $0 < f \le 1000$ and $0.5 \le (a+b+c)/f \le 1.5$;

n is a number which satisfies the condition $1 \le n \le 3$, with (B) one or more compounds which are chosen from the compounds terminated by an alkenyl group of general formulae (8), (9), (10), (11) and (12) below $$CH_2{=}CH{-}C_lH_{2l}{-}O{-}(CH_2CH(OH)CH_2O)iR^4 \quad (8)$$

$$CH_2{=}CH{-}C_mH_{2m}{-}(SiOR^1_2){-}SiR^1_3{-} \quad (9)$$

$$CH_2{=}CH{-}C_mH_{2m}{-}SiR^1_{k1}{-}(OSiR^1_3)_{3\text{-}k1} \quad (10)$$

$$CH_2{=}CH{-}C_mH_{2m},{-}SiR^1_{k1}{-}(OSiR^1_{k2}(OSiR^13)_{3\text{-}k2})_{3\text{-}k1} \quad (11)$$

$$CH_2{=}CH{-}C_mH_{2m}{-}SiR^1k^1{-}(OSiR^1_{k2}(OSiR^1_{k3}(OSiR^1_{k3})_{3\text{-}k3})_{3\text{-}k2})_{3\text{-}k1} \quad (12)$$

Where $R^4$ is a substituted or unsubstituted monovalent hydrocarbon group or a hydrogen atom, the indices I and i are numbers which satisfy the conditions $0 \le I \le 15$ and $0 < i \le 5$;

the indices m, j and $k_1$ to $k_3$ are numbers which satisfy the conditions $0 \le m \le 5$, $0 \le j \le 500$, $0 \le k_1 \le 2$, $0 \le k_2 \le 2$ and $0 \le k_3 \le 2$; said comprise a compound of general formula (8).

The organosilicon resin containing hydrosilyl groups of mean composition formula (7) and the compound having terminal alkenyl groups of general formula (8), (9), (10),

(11) or (12) are mixed in a molar ratio, expressed as hydrosilyl groups/terminal unsaturated groups, which is preferably from 0.5 to 2.0 and more preferentially from 0.8 to 1.2.

The addition reaction is preferably carried out in the presence of a platinum or rhodium catalyst. Specific examples include chloroplatinic acid, chloroplatinic acid modified by an alcohol and chloroplatinic acid/vinylsiloxane complexes. When an excessive amount of catalyst is included, a discoloration of the sample is produced, and thus the amount of platinum or of rhodium is preferably 50 ppm or less and more preferably 20 ppm or less.

In addition, if necessary, the addition reaction can be carried out in the presence of an organic solvent. Mention may be made, among the examples of organic solvent, of cyclic organopolysiloxanes, such as octamethylcyclotetrasiloxane, decamethylcyclopentasiloxane and dodecamethylcyclohexasiloxane; aromatic hydrocarbons, such as toluene and xylene; solvents of ketone type, such as acetone, methyl ethyl ketone, diethyl ketone and methyl isobutyl ketone; aliphatic hydrocarbons, such as hexane, heptane, octane and cyclohexane; and aliphatic alcohols, such as methanol, ethanol, 1-propanel, 2-propanol, 1-butanol, 2-methyl-1-propanol, 2-butanol, 2-methyl-2-propanol, 1-pentanol, 2-methylbutanol, 2-pentanol, 1-hexanol, 2-methylpentanol, 1-heptanol, 1-octanol, 1-nonanol, 1-decanol, phenol, benzyl alcohol, ethylene glycol and 1,2-propylene glycol. From the viewpoint of the reactivity, ethanol, 1-propanol and 2-propanol are preferred.

The amount of solvent used is preferably from 1% to 80% and more preferably from 5% to 50% of the overall reaction system. In the above range, the reaction system is kept uniform and the reaction takes place efficiently.

The conditions of the addition reaction are not particularly limited, although heating at reflux at a temperature of between 5° and 150° C., in particular between 8° and 120° C., for approximately 1 to 10 hours is preferred.

After the addition reaction, the stage of removal of the rhodium or platinum catalyst used with activated carbon can be included. The amount of activated carbon used is preferably from 0.001% to 5.0% and in particular from 0.01% to 1.0% of the overall system. The discoloration of the sample can be better suppressed by fixing the amount of activated carbon in this range.

After the addition reaction, if necessary, the stage of removal of the remaining hydrosilyl groups can be included. In particular in the cases where use in applications such as cosmetic preparations is anticipated, there exists a possibility of these hydrosilyl groups becoming deactivated over time due to dehydrogenation reactions, which presents a problem from the viewpoint of safety. It is thus preferable to include a stage of maintenance of the hydrosilyl groups.

An example of stage of removal of the hydrosilyl groups is the process of hydrolysis of the unreacted hydrosilyl groups by the addition of a basic catalyst, such as an alkali metal carbonate, an alkali metal bicarbonate or an alkali metal hydroxide, and then neutralization by the addition of an amount of acid catalyst equal to the molar equivalent of the basic catalyst. Specific examples of the basic catalyst comprise strong basic catalysts, such as lithium hydroxide, sodium hydroxide, potassium hydroxide, calcium hydroxide and barium hydroxide; and weak basic catalysts, such as sodium carbonate, calcium carbonate and sodium bicarbonate. From the viewpoint of the promotion of the dehydrogenation reaction, the use of a strong basic catalyst is particularly preferred, sodium hydroxide being particularly preferred. Mention may be made, among acid catalysts, of hydrochloric acid, sulfuric acid, sulfurous acid, fuming sulfuric acid, oxalic acid, p-toluenesulfonic acid, methanesulfonic acid, trifluoroacetic acid, trifluoromethanesulfonic acid, phosphoric acid, formic acid, acetic acid, propionic acid, benzoic acid and citric acid. In general, instead of using the acid alone or the base alone, it is preferable to use them with water and to heat them to a temperature which is not greater than the boiling point of water.

After the addition reaction, if necessary, the stage of deodorization to reduce the odor can be included. When use in applications such as cosmetic preparations in particular is anticipated, because the product acquires an odor with time, it is preferable to include a stage of deodorization. The mechanism for the deodorization of ordinary silicones modified by polyethers can be explained as follows. When an addition reaction between a polyether etherified by allyl groups and a hydropolyorganosiloxane is carried out in the presence of a platinum catalyst, the allyl groups rearrange internally in the form of side reactions, forming a polyether etherified by propenyl groups. This propenyl-etherified polyether has no reactivity with the polyorganosiloxane hydrogen and thus remains in the system as an impurity. It is believed that when water acts on this propenyl-etherified polyether, the propenyl ether hydrolyzes, giving rise to propionaldehyde, which gives off an unpleasant odor. It is known that the above hydrolysis reaction is also promoted in the presence of an acid catalyst. Consequently, when the silicone modified by a polyether is used in a water-based cosmetic preparation, due to the oxidative deterioration of the polyether, the preparation tends to become acidic with time, promoting the hydrolysis reaction described above and bringing about the appearance of a bad odor.

Typical examples of the stage of deodorization comprise two approaches. The first is that in which, by adding an acid catalyst to the solution after the addition reaction, any propenyl ether remaining in the system is hydrolyzed and the propionaldehyde which is formed is removed by strip purification (JP No. 2137062).

Specific examples of the acid catalyst used in the first approach comprise hydrochloric acid, sulfuric acid, sulfurous acid, fuming sulfuric acid, oxalic acid, p-toluenesulfonic acid, methanesulfonic acid, trifluoroacetic acid, trifluoromethanesulfonic acid, phosphoric acid, formic acid, acetic acid, propionic acid, benzoic acid and citric acid. These acids are used in combination with water. In the case where it is necessary to remove the acid which has been used, it is preferable to use an acid having a low boiling point, such as hydrochloric acid, formic acid, acetic acid or trifluoroacetic acid. Likewise, from the viewpoint of the effectiveness of the treatment, it is preferable to use a strong acid, such as hydrochloric acid or trifluoroacetic acid.

The treatment temperature is preferably fixed at 80° C. or less in order to prevent the oxidation of the hydrophilic groups. The amount of acidic aqueous solution added is preferably fixed from 0.1% to 100%, with respect to the organosilicon resin modified by organic groups. The use of 5% to 30% is more preferred.

From the viewpoint of the productivity, the process consisting of adding an aqueous solution to the post reaction solution so as to regulate the pH at 7 or less and of carrying out a strip purification after stirring under heating is preferred. The purification of the strip can be carried out at normal temperature or under reduced pressure. The temperature conditions are preferably fixed at 120° C. or less. In order to efficiently purify the strip under these temperature conditions, it is preferable to carry out this operation under reduced pressure; when it is carried out at normal pressure, the operation is preferably carried out under a stream of inert gas, such as nitrogen or argon.

The second approach is that in which, by adding hydrogen to the solution after the addition reaction, the unsaturated double bonds are alkylated (subjected to a hydrogenation reaction) and the formation of propionaldehyde over time is controlled in a stable manner (U.S. Pat. No. 5,225,509; JP-A H07-330907).

The hydrogenation reactions comprise methods involving the use of hydrogen and methods involving the use of metal hydrides, and there also exist homogeneous reactions and heterogeneous reactions. These methods can be used alone but it is also possible to use in them combination. However, given the advantage that there is no trace of catalyst used in the product, a heterogeneous catalytic hydrogenation reaction using a solid catalyst is preferred.

The solid catalyst is, for example, nickel, palladium, platinum, rhodium, cobalt, chromium, copper, iron and others, in the uncombined form or in the compound form. In this case, it is not necessary to use a catalyst support. However, when a catalyst support is used, the support can, for example, be activated carbon, silica, silica/aluminum, aluminum or zeolite. These catalysts can be used alone but it is also possible to use them in combination. The preferred catalyst is Raney nickel, which is economically advantageous. As the Raney nickel is generally developed and used with an alkali, it is necessary to carefully measure the pH of the reaction system. Furthermore, the reaction system becomes weakly alkaline, which is particularly effective for the deodorization when the hydrolysis reaction is carried out with an acidic aqueous solution.

It is preferable to carry out the hydrogenation reaction at a pressure generally of between 1 and 100 MPa and between 5° and 200° C. The hydrogenation reaction can be carried out batchwise or continuously. When it is a noncontinuous process, the reaction time depends, for example, on the amount of catalyst and on the temperature but it is generally of between 3 and 12 hours. The hydrogen pressure can be adjusted to an appropriate fixed pressure. The final point of the hydrogenation reaction is the point at which the hydrogen pressure has ceased to change and it can thus be determined by carefully monitoring a manometer.

The amount of aldehyde included in the glycerolated silicone resin which has been purified by this acid treatment and this hydrogenation treatment can be fixed at 70 ppm or less, preferably at 20 ppm or less and more preferably at 10 ppm or less.

It is also possible to combine both types of abovementioned deodorization stages. In the approach which involves an acid treatment, the decomposition and the removal of the aldehyde compound is possible but, as there is a limit to the complete removal of the unsaturated double bonds, the formation of odorous aldehyde from that cannot be completely suppressed. In the approach which involves a hydrogenation reaction, by eliminating the unsaturated double bonds, it is possible to reduce the amount of aldehyde compound which is formed because of that. However, the aldehyde condensate which is formed with the condensation of a portion of the aldehyde remains in the system even after such a treatment has been carried out and the removal by strip purification is also difficult. Consequently, by alkylating the unsaturated double bonds which remain when the solution, following the addition reaction, is subjected to hydrogenation, and by subsequently decomposing the aldehyde condensate in the system by adding an acid catalyst, complete deodorization is possible (WO2002/05588).

The weight-average molecular weight of the glycerolated silicone resin of mean formula (1) preferably varies from 1000 to 100,000; from the viewpoint of the performance qualities and of the ease of the operations, such as the filtration, the weight-average molecular weight preferentially varies from 3000 to 50,000. Here and subsequently, the weight-average molecular weight can be determined as the polystyrene-equivalent weight-average molecular weight in gel permeation chromatography (GPC).

The glycerolated silicone resin according to the invention is in a form at 25° C. which can be solid or liquid; from the viewpoint of the formability of the film, it is preferably solid.

In particular, the glycerolated silicone resin according to the invention of formula (1) for which the indices b and c satisfy the conditions $0<b\leq 30$ and $0\leq c\leq 30$, the index i in the general formula (2) is a number which satisfies the condition $0<i\leq 3$ and the index j in the general formula (3) satisfies the condition $0\leq j\leq 10$ is the form of a solid at 25° C. and preferably exhibits a weight-average molecular weight which preferably varies from 1000 to 100 000 and more preferentially from 3000 to 50,000.

The glycerolated silicone resins according to the invention have a hydrophilic-lipophilic balance (HLB), as determined by the Griffin formula, preferably of 0.1 to 15 and more preferably of 1.0 to 8.0.

According to a preferred form, the composition of the invention comprises at least one glycerolated silicone resin in the formula (1) of the (3-Glycidoxypropyl) Dimethylsiloxy Trimethylsiloxysilicate type corresponding to the following formula (21):

$$[(CH_3)_3SiO_{1/2}]_a[R(CH_3)_2SiO_{1/2}]_b(SiO_{4/2})_f \quad (21)$$

Where

R denotes the 3-glycidoxypropyl group of structure $$C_3H_6OCH_2—CH(OH)CH_2OH;$$

the indices a, b and f are numbers which satisfy the conditions $0\leq a\leq 400$, $0<b\leq 30$, $0<f\leq 1000$ and $0.5\leq(a+b)/f\leq 1.5$.

According to a particularly preferred form, the glycerolated silicone resin of the (3-Glycidoxypropyl) Dimethylsiloxy Trimethylsiloxysilicate type of formula (21) is in the form of a solution in at least one volatile oil.

The term "volatile oil" is understood to mean, within the meaning of the invention, any oil capable of evaporating on contact with the skin in less than one hour, at ambient temperature and atmospheric pressure. The volatile oil is a volatile cosmetic compound, liquid at ambient temperature, having in particular a non-zero vapor pressure, at ambient temperature and atmospheric pressure, in particular having a vapor pressure ranging from 2.66 Pa to 40 000 Pa, in particular ranging from 2.66 Pa to 13,000 Pa and more particularly ranging from 2.66 Pa to 1300 Pa.

The volatile oil in accordance with the invention can be chosen from the group constituted of hydrocarbon oils, silicone oils and their mixtures.

The term "hydrocarbon oil" is understood to mean an oil containing predominantly hydrogen and carbon atoms and optionally one or more functions chosen from hydroxyl, ester, ether and carboxyl functions.

Within the meaning of the present invention, the term "silicone oil" denotes an oil comprising at least one Si—O group and more particularly an organopolysiloxane.

The volatile hydrocarbon oils which can be used in the compositions according to the invention can be chosen from branched C8-C16 alkanes.

Mention may in particular be made, as C8-C16 isoalkanes of petroleum origin (also known as isoparaffins), such as isododecane (also known as 2,2,4,4,6-pentamethylheptane), isodecane, isohexadecane and, for example, the oils sold under the Isopar® or Permethyl® tradenames. More preferentially, isododecane will be used.

Mention may be made, by way of example of volatile silicone oil which can be used in the invention, of volatile silicone oils, such as volatile linear or cyclic silicone oils, in particular those having a viscosity of 2 to 8 centistokes ($2.10^{-6}$ to $8.10^{-6}$ $m^2/s$) and containing in particular from 2 to 7 silicon atoms, these silicones optionally comprising alkyl or alkoxy groups containing from 1 to 10≤carbon atoms. Mention may in particular be made, as volatile silicone oils which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane; and their mixtures. More preferentially, decamethylcyclopentasiloxane ($D_5$) will be used.

According to a particularly preferred form, the glycerolated silicone resin of the (3-Glycidoxypropyl) Dimethylsiloxy Trimethylsiloxysilicate type of formula (21) is in the form of the solution comprising 49.5% by weight of active material in isododecane, such as the product manufactured under the tradename X-25-9138A® by SHIN ETSU with a weight-average molecular weight of 11,000.

Preferably, the weight ratio of active material of (1) silicone acrylate copolymer to (2) glycerolated silicone resin is from about 15:1 to about 1:15, from about 10:1 to about 1:10, from about 5:1 to about 1:5, from about 3:1 to about 1:3, from about 2:1 to about 1:2, from about 1.5 to 1 to about 1:1.5, and about 1:1 including any ratio ranges discerned from the examples of the present specification. Preferably, more silicone acrylate copolymer is present in the compositions of the present invention than glycerolated silicone resin.

Oil Phase

According to preferred embodiments of the present invention, compositions further comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |
| Undecane | 62 |
| Tridecane | 94 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, *quinoa* oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R^5COOR_6$ in which $R^5$ represents a linear or branched higher fatty acid residue containing from 1 to 40 carbon atoms, including from 7 to 19 carbon atoms, and $R^6$ represents a branched hydrocarbon-based chain containing from 1 to 40≤carbon atoms, including from 3 to 20≤carbon atoms, with $R_6+R_7\geq 10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40≤carbon atoms;

$C_8$ to $C_{26}$ fatty alcohols, for instance oleyl alcohol, cetyl alcohol, stearyl alcohol, and cetearyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

Further, examples of non-volatile oils that may be used in the present invention include, but are not limited to, silicone oils such as dimethicone (polydimethylsiloxane) of various viscosities as well as phenylated silicone oils such as phenyl trimethicone and trimethylsiloxyphenyl dimethicone.

According to preferred embodiments, if present, the at least one oil is present in the compositions of the present invention in an amount ranging from about 5 to about 80% by weight, more preferably from about 10 to about 70% by weight, and most preferably from about 15 to about 60% by weight, based on the total weight of the composition, including all ranges and subranges within these ranges.

According to preferred embodiments of the present invention, the compositions of the present invention further comprise at least one wax. Suitable examples of waxes that can be used in accordance with the present disclosure include those generally used in the cosmetics field: they include those of natural origin, such as beeswax, carnauba wax, candelilla wax, ouricury wax, Japan wax, cork fibre wax or sugar cane wax, rice bran wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosenyl stearate, glycerides which are concrete at 30° C., for example at 45° C.

According to particularly preferred embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di)methylsiloxane esters which are solid at 30° C. and whose ester chain comprising at least 10≤carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40≤carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 allyldimethylsilyl polypropylsilsesquioxane; and mixtures thereof.

According to preferred embodiments, the compositions of the present invention contain less than 1% wax.

According to preferred embodiments, the compositions of the present invention contain less than 0.5% wax.

According to preferred embodiments, the compositions of the present invention contain no wax.

If present, the wax or waxes may be present in an amount ranging from 1 to 30% by weight relative to the total weight of the composition, for example from 2 to 20%, and for example from 3 to 10%, including all ranges and subranges therebetween.

Optional Ingredients

Block Copolymer

According to embodiments of the present invention, compositions optionally containing at least one block copolymer are provided. The block copolymers are characterized by the presence of at least one "hard" segment, and at least one "soft" segment. Aside from their compositional nature, the hard and soft segments of the block copolymers are defined in terms of their respective glass transition temperatures, "$T_g$". More particularly, the hard segment has a $T_g$ of about 50° C. or more, whereas the soft segment has a $T_g$ of about 20° C. or less. The glass transition temperature $T_g$ for the hard block can range from about 50° C. to about 150° C.; about 60° C. to about 125° C.; about 70° C. to about 120° C.; or about 80° C. to about 110° C. The glass transition temperature $T_g$ for the soft segment of the Glycerolated silicone resin can range from about 20° C. to about −150° C.; about 0° C. to about −135° C.; about −10° C. to about −125° C.; and about −25° C. to about −100° C. A more in depth explanation can be found in U.S. Pat. Nos. 5,294,438 and 6,403,070, the entire contents of which are hereby incorporated by reference.

The block copolymer is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The block copolymer comprises at least one hard segment which is styrene.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymer enhances the integrity of the film formed.

Although the block copolymers may comprise styrene, it is preferred that the styrene content of the block copolymer be less than 40% by weight, preferably less than 30% by weight, and more preferably less than 20% by weight, based on the weight of the block copolymer, and preferably greater than 5% by weight, preferably greater than 7% by weight, and preferably greater than 10% by weight, including all ranges and subranges therebetween such as, for example, 10%-30%, 6%-22%, 5%-40%, etc. This is because of the tendency of block copolymers having a styrene content of greater than 40% by weight to harden/gel in conventional carrier systems. However, in the event that a block copolymer having a styrene content of greater than 40% by weight is used, it may be necessary to also employ a co-solvent or functional ingredient capable of dissolving a styrene block in an amount effective to control the hardening/gelling of the styrene-containing compound in the composition.

A particularly preferred block copolymer is a combination of di-block and tri-block copolymers of styrene-ethylene/butylene-styrene (SEBS), commercially available from Shell Chemical Company under trade name Kraton G1657M. It should be noted, however, that any thermoplastic elastomer of the block copolymer type having at least one soft and at least one hard segment may be used without departing from the spirit of the invention.

The block copolymer will preferably have a solubility parameter, relative to the tackifier component, of δ±2, more preferably δ±1.7, more preferably δ±1.5, more preferably δ±1.3, more preferably δ±1.0, more preferably δ±0.7, more preferably δ±0.5, and more preferably δ±0.3.

The block copolymer, if present, is preferably present in the compositions of the present invention in an active solid content amount ranging from about 0.5% to about 30%, preferably from about 0.75% to about 20%, and preferably from about 1% to about 10%, by weight with respect to the total weight of the composition, including all ranges and subranges therebetween. According to preferred embodiments, compositions of the present invention contain at least about 2% by weight of the total weight of the composition, preferably at least about 5% by weight of the total weight of the composition, of the block copolymer. It is to be understood that acceptable ranges of block copolymer present in the invention compositions include 2%-30%, 2%-20%, 2%-10%, 2%-5%, 5%-30%, 5%-20%, and 5%-10% by weight based on the weight of the composition.

However, according to some preferred embodiments, the compositions of the present invention contain less than 0.1% block copolymer(s), preferably less than 0.05% block copolymer(s), and preferably no block copolymer(s).

Tackifiers

According to preferred embodiments of the present invention, compositions of the present invention may optionally further comprise at least one tackifier. Tackifiers may be present in compositions of the present invention even if the compositions do not also contain a block copolymer as described above.

A substance is described as a tackifier if, by adding it to a block copolymer, the resulting composition has the properties of a pressure sensitive adhesive. In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant, for example, that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter 6 according to the Hansen solubility space is defined in the article "*Solubility Parameter Values*" by Eric A. Grulke in the work "*Polymer Handbook*" 3rd edition, Chapter VII, pages 519-559, the entire content of which is hereby incorporated by reference, by the relationship:

$$\delta = (d_D{}^2 + d_P{}^2 + d_H{}^2)^{1/2},$$

$d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like). The definition of the solvents in the three-dimensional solubility space according to Hansen is given in the article by C. M. Hansen: "*The three-dimensional solubility parameters*" J. Paint Technol., 39, 105(1967), the entire content of which is hereby incorporated by reference.

The at least one tackifier used in the present invention preferably has a solubility parameter corresponding to 6 and the block copolymer preferably has at least one segment whose solubility parameter corresponds to δ±2, preferably δ±1.7, more preferably δ±1.5, more preferably δ±1.3, more preferably δ±1.0, more preferably δ±0.7, more preferably δ±0.5, and more preferably δ±0.3.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar, where "non-polar" means that the tackifier is substantially free of monomers having polar groups. Preferably, polar groups are not present; however, if they are present, they are preferably present in an amount of up to about 5% by weight, preferably up to about 2% by weight, and more preferably up to about 0.5% by weight.

In preferred embodiments, the tackifier may have a softening point (Ring and Ball, as measured by ASTM E-28) of about 80° C. to about 150° C., preferably about 100° C. to about 130° C. In other preferred embodiments, the tackifier may be liquid and have an R and B softening point of between about −70° C. and about 70° C.

According to preferred embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name Regalite©. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

A particularly preferred tackifier for use in the present invention is a hydrogenated hydrocarbon resin such as, for example, a hydrogenated styrene/methyl styrene/indene copolymer, commercially available from Eastman under the tradename Regalite® R1100.

According to particularly preferred embodiments, the compositions of the present invention comprise an equivalent amount of the at least one block copolymer and the at least one tackifier, or more of the at least one block copolymer as compared to the at least one tackifier. For example, the at least one block copolymer and the at least one tackifier can be present in ratios of 1.25, 1.00, 0.75, 0.50, 0.33, 0.25, and 0.10, including all ranges and subranges therebetween, with ratios from 1.00 to 0.33 being particularly preferred.

If present in the compositions of the present invention, the tackifier(s) are preferably present in an amount of from about 0.1 to about 10 percent by weight, preferably from 1 to 10 percent by weight, preferably from 1 to 8 percent by weight and preferably from 1 to 5 percent by weight of the total weight of the composition, including all ranges and subranges therebetween However, according to other preferred embodiments, the compositions of the present invention contain less than 0.1% tackifier(s), preferably less than 0.05% tackifier(s), and preferably no tackifier(s).

Coloring Agents

According to preferred embodiments of the present invention, compositions of the present invention may optionally further comprise at least one coloring agent. According to this embodiment, the coloring agent(s) is/are preferably chosen from pigments, dyes, nacreous pigments, pearling agents, and mixtures thereof.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 40% by weight of the total weight of the composition, such as from 0.0001% to 30%, including all ranges and subranges therebetween.

The nacreous pigments which may be used according to the present invention may be chosen from colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.0001% to 40%, preferably from 0.001% to 30%, including all ranges and subranges therebetween.

The pigments, which may be used according to the present invention, may be chosen from white, colored, inorganic, organic, polymeric, and nonpolymeric pigments. Representative examples of mineral pigments include titanium dioxide, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.0001% to 40%, and further such as from 0.001% to 30%, including all ranges and subranges therebetween.

Aqueous Phase

The compositions of the present invention may also optionally contain water. When the compositions of the present invention contain water, they are preferably in the form of an emulsion. Preferably, when the compositions of the present invention contain water, they are in the form of an oil-in-water emulsion (O/W) or a water-in-oil emulsion (W/O). Preferably, when in the form of an emulsion, the oil phase contains predominantly silicone oils (Si/W or W/Si emulsion) or hydrocarbon oils. When present, water is preferably present in an amount of from about 10% to about 80% by weight, preferably from about 20% to about 70% by weight, preferably from about 35% to about 65% by weight, including all ranges and subranges therebetween, all weights being based on the total weight of the composition.

According to preferred embodiments, however, compositions of the present invention are devoid of water, substantially free of water, or free of water as defined herein. Preferably, the compositions of the present invention are anhydrous.

The composition of the invention can also comprise any additive usually used in the field under consideration. For example, additional film formers other than the at least one silicone acrylate and the at least one Glycerolated silicone resin, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the keratinous materials of human beings such as, for example, lips, skin or eyelashes.

In particular, suitable gelling agents for the oil phase include, but are not limited to, lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, 2nd edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

Preferably, the gelling agent, if present, is present in the composition of the present invention in amounts of active material generally ranging from about 0.1% to about 10%, preferably from about 0.25% to about 5%, and more preferably from about 0.5% to about 3.5%, by weight, based on the total weight of the composition, including all ranges and subranges in between.

According to preferred embodiments of the present invention, methods of treating, caring for and/or making up a keratinous material by applying compositions of the present invention to the keratinous material in an amount sufficient to treat, care for and/or make up the keratinous material are provided. Preferably, "making up" the keratinous material includes applying at least one coloring agent to the keratinous material in an amount sufficient to provide color to the keratinous material.

According to yet other preferred embodiments, methods of enhancing the appearance of a keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratinous material in an amount sufficient to treat, care for and/or make up the keratinous material, to cover or hide defects associated with keratinous material, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

According to preferred embodiments of the present invention, methods of increasing color stability of a colored composition comprising combining at least one silicone acrylate copolymer and at least one glycerolated silicone resin in the composition in amounts and ratios indicated in the description above so as to increase color stability of the composition are provided. Preferably, such compositions are anhydrous. Preferably, such compositions $d_D$ not contain film-forming effective amounts of silicone resins which have not been glycerolated, and are preferably free of silicone resins which have not been glycerolated. Also preferably, such compositions are liquid.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Inventive Compositions

The following compositions, both a general formulation and a more specific formulation, can be prepared:

| General Formula | | Phase | More Specific Formula |
|---|---|---|---|
| 5-25% | ACRYLATES/DIMETHICONE COPOLYMER (40% active) | Phase A | 10-15% |
| 5-20% | GLYCERIN-MODIFIED MQ (50% active) IN ISODODECANE (50%) | | 10-15% |
| 1-20% | Volatile Hydrocarbon Oil | Phase B | 10-15% |
| 1-20% | Phenylated Silicone Oil | | 10-15% |
| 1-15% | Non-Phenylated Silicone Oil | | 2-7% |
| 1-10% | Non-Volatile Hydrocarbon Oil | | 1-5% |
| 1-10% | Tackifier | | 1-5% |
| 1-15% | Non-Phenylated Silicone Oil | Phase C | 5-10% |
| 1-20% | Pigment | Phase D | 10-20% |
| 1-20% | Wax | Phase E | 10-20% |
| 1-10% | Emollient | Phase F | 1-5% |
| | | Total: | 100 |

To prepare the above formulations, phases B-F can be combined and heated to 90° C. until ingredients have melted.

Then, phase A can be added, after which the composition can be mixed for approximately 1 minute at 2350 rpm until homogenous.

Example 2—Multichallenge Wear Assay Test

Simplex systems containing various film formers, pigment, isododecane and thickener were prepared. The only variable in these systems was the type of film former present.

Comparative Sample 1 contained non-glycerolated silicone resin (polypropylsilsesquioxane) and silicone acrylate copolymer (KP550).

Comparative Sample 2 contained non-glycerolated silicone resin (trimethylsilioxysilicate) and silicone acrylate copolymer (KP550).

Inventive Sample 3 contained glycerolated silicone resin and silicone acrylate copolymer (KP550).

Comparative Sample 4 contained only silicone acrylate copolymer (KP550).

These compositions were tested as follows in a multichallenge wear test. A film was deposited onto a surface such as a black bykochart Black Scrub Panels P121-1 ON #5015 using a 1 mL drawdown bar. After drying over night at 37° C., the deposit was covered with olive oil, artificial saliva or acetic acid). The film was wiped by hand with an absorbent material such as cotton or kimwipe. It was determined how much of the sample remained undisrupted on the scrub panel as well as how much of the sample was transferred to the absorbent material using a numerical scale of 1-3, where 1=least transfer/best film property and 3=most transfer/worst film property. This testing was performed twice, and an average score was determined. Results are present in the following Table.

| Sample | Oil | Oil KW | Saliva | Saliva KW | Acetic Acid | A.A. Wipe | Oil | Oil KW | Saliva | Saliva KW | Acetic Acid | A.A. Wipe | ASTM | avg |
|---|---|---|---|---|---|---|---|---|---|---|---|---|---|---|
| 1 | 2.00 | 3.00 | 1.00 | 1.25 | 1.00 | 1.75 | 2.00 | 3.00 | 1.00 | 1.25 | 1.00 | 1.75 | 1.0 | 1.62 |
| 2 | 1.25 | 1.75 | 1.00 | 1.25 | 1.00 | 1.75 | 1.00 | 1.75 | 1.00 | 1.25 | 1.00 | 1.75 | 1.25 | 1.31 |
| 3 | 1.00 | 1.75 | 1.25 | 1.25 | 1.25 | 1.75 | 1.00 | 1.75 | 1.25 | 1.25 | 1.25 | 1.75 | 1.25 | 1.37 |
| 4 | 1.25 | 3.00 | 1.25 | 1.25 | 1.25 | 1.75 | 1.25 | 3.00 | 1.25 | 1.25 | 1.25 | 1.75 | 1.0 | 1.58 |

Example 3—Stability Testing

Stability testing after 30 minutes was performed as follows. 5 mL of composition was put into a centrifuge tube and centrifuged at 900 rpm for 30 mins. The degree of separation in mL and any color observations were made. The higher the value of separation, the more the sample separated.

Stability testing after 6 months was performed as follows. Samples were allowed to sit at room temperature for 6 months. The degree of separation in mL and any color observations were made. The higher the value of separation, the more the sample separated. Separation, discoloration of the surface, white striations or overcast surface visual appearance was noted.

Samples A-D based on example 1 above were prepared. The only variable in these systems was the type of film former present. Each Sample A-D contained approximately 10% active solid content of the film former(s) identified below. Samples A-C contained the identified film formers in an active solid content ratio of 1:1. Sample D contained only one film former. The differences in film former content were as follows.

| | Sample A | Sample B | Sample C | Sample D |
|---|---|---|---|---|
| POLYPROPYLSILSESQUIOXANE (72%) (and) ISODODECANE | X | | | |
| TRIMETHYLSILOXYSILICATE (and) POLYPROPYLSILSESQUIOXANE | | | | |
| ACRYLATES/DIMETHICONE COPOLYMER (40%) | X | X | X | X |
| TRIMETHYLSILOXYSILICATE (75%) | | X | | |
| GLYCERIN-MODIFIED MQ (50%) IN ISODODECANE (50%) | | | X | |

In particular, after 6 months at room temperature in bulk, Sample A showed separation of liquid and color shifting/striations of color; Sample B showed separation of liquid and also non uniformity of color; Sample C (invention) showed uniform coloration and no separation; and Sample D. showed separation of formulation with time and non-uniformity of color.

Results for all stability testing for these samples are set forth in the Table below.

| | Centrifuge Freshly Made Bulk 30 min mix * 900 g Separation 1 ml | Centrifuge Freshly Made Bulk 30 min mix * 900 g Coloration | Bulk appearance After 6 months at RT |
|---|---|---|---|
| Sample 1 | ~0.9 | Slightly cloudy slight pink hue | Separation Liquid/Shift Color |
| Sample 2 | ~1.25 | opaque slight pink hue | Blue Color separation and uniform color |
| Sample 3 (Inventive) | ~1.25 | Slightly cloudy slight pink hue | Uniform coloration and no separation |
| Sample 4 | ~1.75 | Slightly cloudy slight pink hue | Separation and non uniformity |

What is claimed is:

1. A composition comprising a film forming component comprising (1) at least one silicone acrylate copolymer and (2) at least one glycerolated silicone resin, wherein the composition is devoid of surfactant.

2. The composition of claim 1, wherein the composition is anhydrous.

3. The composition of claim 1, wherein the composition is liquid.

4. The composition of claim 1, wherein the composition further comprises at least one coloring agent.

5. The composition of claim 1, further comprising at least one volatile oil.

6. The composition of claim 1, further comprising at least one phenylated silicone oil.

7. The composition of claim 1, wherein the at least one silicone acrylate copolymer is an acrylates/dimethicone copolymer.

8. The composition of claim 1, wherein the at least one glycerolated silicone resin is a glycerolated MQ resin.

9. The composition of claim 7, wherein the at least one glycerolated silicone resin is a glycerolated MQ resin.

10. A method of making up lips comprising applying the composition of claim 1 to lips in an amount sufficient to makeup the lips.

11. The composition of claim 1, wherein the composition contains less than 0.5% water by weight with respect to the total weight of the composition.

12. The composition of claim 1, wherein the composition is devoid of water.

13. The composition of claim 1, wherein the composition is not in the form of an emulsion.

14. The composition of claim 1, wherein the film forming component further comprises at least one additional film former.

15. The composition of claim 1, wherein the at least one silicone acrylate copolymer is a dendrimer copolymer.

16. The composition of claim 1, wherein the composition contains less than 1% of wax by weight with respect to the total weight of the composition.

* * * * *